United States Patent
Lefloch et al.

(10) Patent No.: US 8,926,821 B2
(45) Date of Patent: Jan. 6, 2015

(54) USE OF DIAZONIUM SALTS FOR THE FORMATION OF THICK LAYERS ON AT LEAST ONE SURFACE OF A SUBSTRATE

(75) Inventors: Fabien Lefloch, Rennes (FR); Muriel Matheron, Chambery (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 57 days.

(21) Appl. No.: 13/820,325

(22) PCT Filed: Aug. 31, 2011

(86) PCT No.: PCT/IB2011/053815
§ 371 (c)(1),
(2), (4) Date: May 13, 2013

(87) PCT Pub. No.: WO2012/029035
PCT Pub. Date: Mar. 8, 2012

(65) Prior Publication Data
US 2013/0239661 A1   Sep. 19, 2013

(30) Foreign Application Priority Data
Sep. 1, 2010   (FR) ..................... 10 03498

(51) Int. Cl.
C25D 9/02      (2006.01)
G01N 27/28     (2006.01)
C07C 255/34    (2006.01)
C09D 5/44      (2006.01)
G01N 33/00     (2006.01)
B05D 1/00      (2006.01)

(52) U.S. Cl.
CPC .............. G01N 27/28 (2013.01); C07C 255/34 (2013.01); C09D 5/4476 (2013.01); G01N 33/0047 (2013.01); C25D 9/02 (2013.01); B05D 1/007 (2013.01); C07C 2103/18 (2013.01)
USPC .......................................................... 205/317

(58) Field of Classification Search
CPC ....................................................... C25D 9/02
USPC .......................................................... 205/317
See application file for complete search history.

(56) References Cited

FOREIGN PATENT DOCUMENTS

EP   1 632 814    3/2006
WO   03/018212    3/2003

OTHER PUBLICATIONS

International Search Report mailed Jan. 18, 2012 for PCT/IB2011/053815, citing the above reference(s).
Written Opinion from the ISA mailed Jan. 18, 2012 for PCT/IB2011/053815, citing the above reference(s).
Bernard, Marie-Claude et al: "Organic Layers Bonded to Industrial, Coinage, and Noble Metals through Electrochemical Reduction of Aryldiazonium Salts", Chemistry of Materials, vol. 15, No. 18, 2003, 3450-3462 ISSN: 0897-4756.
Hee Kwon Jun et al; "Electrical properties of polypyrrole gas sensors fabricated under various pretreatment conditions", Sensors and Actuators B, Elsevier Sequoia S.A., Lausanne, CH, vol. 96, No. 3, Dec. 1, 2003, pp. 576-581, ISSN:0925-4005.
David James et al: "Chemical Sensors for Electronic Nose Systems", Microchimica ACTA; An International Journal on Micro and Traceanalysis, Springer-Verlag, VI, vol. 149, No. 1-2, Feb. 1, 2005, pp. 1-17, ISSN: 1436-5073.

*Primary Examiner* — Robert Havlin
(74) *Attorney, Agent, or Firm* — Lowe Hauptman & Ham, LLP

(57) ABSTRACT

The invention relates to the use of diazonium salts for the formation of thick layers on at least one surface of a substrate. The diazonium salts used in the invention have the following formula (I): wherein R is a group that can be electrochemically reduced in a reversible manner to a cathodic potential between 0 and −1.5 V, E is a spacer chain consisting of at least one aromatic cyclic group having between 5 and 6 links, optionally containing at least one heteroatom preferably selected from N, S, O or P and optionally substituted by at least one group selected from the $C_1$-$C_5$ alkyls and the halogens, r is 1 or 2, m is a whole number between 1 and 5 inclusive, p is a whole number between 1 and 5, and B is a counter-ion. The invention can be especially applied to the field of gas sensors.

5 Claims, 4 Drawing Sheets

Figure 1:
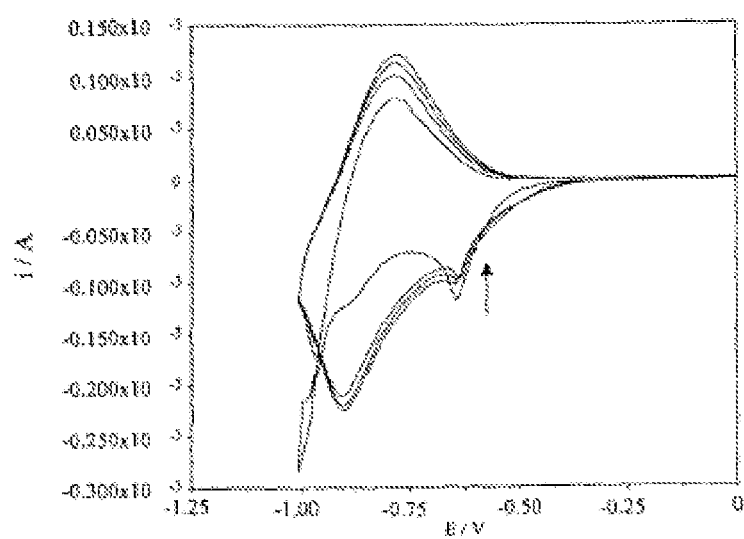

USE OF DIAZONIUM SALTS FOR THE FORMATION OF THICK LAYERS ON AT LEAST ONE SURFACE OF A SUBSTRATE

CROSS REFERENCE TO RELATED APPLICATION

This application claims the priority of French Patent Application No. 1003498, filed on Sep. 1, 2010 in the INPI (French Intellectual Property Office). Further, this application is the National Phase application of International Application No. PCAT/IB2011/053815 filed Aug. 31, 2011, which designates the United States and was published in French.

The invention relates to the use of diazonium salts for the formation of thick layers on at least one surface of a substrate.

It also relates to a diazonium salt and a substrate comprising a thick layer obtained from this diazonium salt.

Finally, it relates to a device for detecting and/or quantifying and/or separating gases and/or volatile organic compounds (VOCs).

Environmental pollution has greatly increased over the past few decades, and volatile organic compounds (VOCs) are acknowledged to be the main cause of current domestic diseases. Indeed, they can cause and worsen certain conditions, including allergies, asthma, cancer and emphysema. Consequently, it is necessary and of great interest to develop efficient sensors capable of directly detecting a large number of gases and/or volatile organic compounds (VOCs).

The article by D. James et al., Microchimica Acta 149, 1-17 (2005), describes systems called "electronic noses", used for detecting and analyzing odors. These systems use chemical sensors which are transducers that integrate chemical interactions into electrical signals. These "electronic noses" are used for applications ranging from the food industry to the medical industry, and also including monitoring of the environment and process control. These gas sensors operate by binding molecules to the surface of the device by means of one or more mechanisms including adsorption, absorption or chemisorption. The binding mechanism has important implications for the selectivity and the reversibility of the detection system, given that a strong binding force will lead to poor reversibility. Thus, adsorption results in weak bonds having good reversibility, but low selectivity. Given that it is difficult to simultaneously obtain good selectivity and good reversibility, a compromise is necessary. Alternatively, in the case of a one-off use of a sensor in disposable form, only good selectivity is to be taken into account, the reversibility of the system then being needless.

One category of gas sensors is made up of piezoelectric sensors, based on the fact that certain anisotropic crystals, when they are subjected to a mechanical tension, generate electric dipoles. There are numerous different forms of piezoelectric sensors, such as bulk acoustic wave (BAW) sensors or surface acoustic wave (SAW) sensors. Bulk acoustic wave (BAW) sensors include quartz crystal microbalances (QCMs). These sensors are sensors which are very sensitive to variation in mass, this sensitivity being based on the piezoelectric properties of the quartz crystal. This technique uses the variations in resonance frequency of the crystal to measure the mass present at the surface, the resonance frequency being greatly dependent on changes in mass of the crystal. Quartz crystal microbalances (QCMs) generally comprise electrodes attached to the quartz, said electrodes exerting an alternating current which forces the crystal to oscillate with a fundamental frequency. However, it appears that these gas sensors are influenced by humidity, it being possible for changes in temperature to also have an effect both on the crystal and on its coating.

The article by A. McGill et al., Chemtech, September 2004, 27-37, describes surface acoustic wave (SAW) chemical sensors, these sensors being coated with polymers applied by spraying or by dipping. However, these processes do not make it possible to functionalize selected parts of the sensor, in small dimensions. Furthermore, this article describes specific polymers, such as polysiloxanes, and it appears that one of the drawbacks of this type of polymer concerns the weak wetting properties of the polysiloxanes on the surface acoustic wave (SAW) devices.

Some other gas-detecting devices use sensors comprising a pair of electrodes covered with organic materials, for instance polymers, deposited on the electrodes and between said electrodes, in order to produce an electrical connection between the electrodes. The organic polymers used are sensitive to the presence of gases, since the adsorption of the gases onto the polymer surfaces affects the electrical properties of the polymers. As a result, the presence of a gas can be detected by monitoring, for example, the change in resistance or in resonance frequency of the sensor exposed to said gas. Indeed, these technologies employ thin absorbent layers of selective chemical material for collecting molecules of interest at the interphase of the coated sensor, said layers of selective chemical material allowing direct detection of gases and/or of volatile organic compounds (VOCs).

The nature of the sensitive polymer is adjusted according to the type of detection desired. For example, the article by H.-K. Jun et al., Sensors and Actuators B 96 (2003) 576-581, describes the use of conducting polymers such as polypyrrole, polyaniline and polythiophene, these polymers being commonly considered to be detection materials owing to their ability to detect gases, and to their optimal performance levels at ambient temperature. However, these sensors have the drawback of having a very fragile structure and a tendency to become oxidized.

Indeed, the coatings of the sensors are prepared by chemical oxidation, this reaction often resulting in the oxidation and in the deactivation of the electrically conducting surface of the gas sensor. In addition, these conductive polymers are immobilized at the surface of the gas sensor without establishing a covalent bond, which gives weakly resistant organic films.

Generally, the layers intended for adsorbing or absorbing the analytes are chosen according to the physicochemical interactions that it is desired to favor.

Indeed, the layer at the surface of the sensors makes it possible, on the one hand, to achieve specific recognition of the analyte, or the family of compounds, to be detected and, on the other hand, to increase the absorption capacity of the sensor, its sensitivity and the resolution of the detection.

Specific recognition is obtained through the choice of a molecule or of a family of compounds which interacts with the analyte (the gas compound to be detected) by means of interactions between chemical functions.

In this context, an interaction resulting in the formation of covalent bonds can result in a highly specific recognition.

On the other hand, it will not make it possible to produce reversible recognition enabling the sensor to be reused.

Thus, in order to develop reversible interactions, it is more judicious to favor weak bonds (the energy of which is less than 100 kJ/mol) such as hydrogen bonds or bonds obtained via Van der Waals forces.

At the current time, it is difficult to obtain layers, in particular from aryl diazonium salts, with a thickness typically greater than 10 nm.

The electrografting of organic layers based on the reduction of diazonium salts is a preferred approach for localized functionalization which can be carried out on a nano electromechanical system (NEMS) scale. The results of the electrografting (layer thickness, potentials to be applied) depend both on the electronic and steric parameters of the molecules used and on the conductivity parameters of the substrates linked to the surface effects. The electrografting of diazoniums is a self-limiting process which makes it possible to form layers of small thicknesses.

This is because electrografting using diazonium salts most commonly leads to layer thicknesses of at most 10 nm since the reduction of the diazonium group results in the creation of radical aryl species which react very rapidly by grafting to the surface of the electrode or by forming dimers. The layer thus created is insulating.

As the grafting takes place, the active surface of the electrode decreases since the grafted areas become passivating and prevent the transfer of electrons from taking place.

Once this blocking effect is achieved, it is impossible to grow the layer since the transfer of electrons is inhibited.

As it happens, for certain gas sensors, for example sensors based on piezoelectric transducers, there is a need to obtain layers with a thickness greater than ten or so nanometers. This is because the signal recorded by these transducers, i.e. the variation in resonance frequency, is proportional to the variation in mass at the surface of the sensor, the latter being proportional to the number of gas or VOC molecules adsorbed within the polymer layer. Thus, the higher the volume of polymer deposited, the greater the recorded signal. Depositing thick polymer layers therefore makes it possible:
  to improve the concentration resolution of the sensor,
  to improve its sensitivity,
  to increase its lifetime (for the case where the gas/polymer interactions are irreversible).

The invention aims to overcome the problems of the prior art and in particular to enable the formation of localized layers with a thickness greater than 10 nm, obtained by electrografting using diazonium salts, on at least one surface, made of a conductive or semiconductive material, of a substrate. This makes it possible to increase the volume of gas-sensitive molecules and thus to increase the absorption capacity of the sensor, i.e. its lifetime (in the case of irreversible interactions) and the possibility of reusing it (in the case of reversible interactions), and also its sensitivity and the detection resolution.

To this effect, the invention proposes using diazonium salts having a chemical group which is stable and electroactive in the cathode potentials, so as to produce an increase in the deposited volume of diazonium salt-based polymers.

The term "electroactive" is intended to mean the property of being activated (oxidized or reduced) by electrochemical reduction or oxidation and, where appropriate, which exhibits reversibility of this activation.

The term "cathode potential" is intended to mean a potential extending from 0 to −1.5 V, relative to the NHE (normal hydrogen electrode), and preferably from 0 to −1.0 V.

This is because the application of higher potentials may be damaging to the substrate.

Thus, the invention proposes the use of at least one compound of general formula I below:

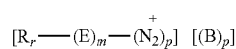

Formula I in which:
  R is a group which can be electrochemically reduced in a reversible manner at a cathode potential of between 0 and −1.5 V,
  E is a spacer chain consisting of at least one 5- to 6-membered aromatic cyclic group optionally containing one or more heteroatoms preferably chosen from N, S, O and P and optionally substituted with one or more groups chosen from $C_1$-$C_5$ alkyls and halogens, r is 1 or 2,
m is an integer between 1 and 5 inclusive,
p is an integer between 1 and 5, and
B is a counterion,
for the formation, by electrografting, of a layer, preferably with a thickness greater than 10 nm, on a surface of a substrate made of a conductive or semi-conductive material.

Preferably, B is chosen from a tosylate, sulfonate, halide or metal chloride group, more preferably B is $PF_6^-$ or $BF_4^-$.

Preferably, R is a group which can be electrochemically reduced in a reversible manner at a cathode potential of between 0 and −1.0 V.

In one preferred embodiment, R is chosen from a dicyanovinylidene, porphyrin, metal porphyrin, fullerene, metal bipyridine complex or quinone group, and a mixture thereof, preferably a dicyanovinylidene group.

A preferred compound of formula I used in the invention is 2-diazonium-9-dicyanofluorenylidene tetrafluoroborate.

However, in one likewise preferred embodiment, a diazonium derivative which is not of formula I is additionally used.

In this case, the diazonium derivative which is not of formula I is preferably chosen from 4-(heptadecafluorooctyl)benzenediazonium tetrafluoroborate, 4-(1,1,1,3,3,3-hexafluoro-2-hydroxypropan-2-yl)benzenediazonium tetrafluoroborate, and mixtures thereof.

The invention also proposes a substrate comprising at least one surface made of a conductive or semiconductive material onto which 9-dicyanofluorenylidene groups are grafted, by covalent bonding.

The invention also proposes a device for detecting and/or quantifying gas compounds and/or volatile organic compounds (VOCs), characterized in that it comprises a substrate comprising at least one surface made of a conductive or semi-conductive material onto which are grafted 9-dicyanofluorenylidene groups, forming a layer with a thickness of greater than 10 nm, which are bonded to said surface of said conductive or semi-conductive substrate by covalent bonding.

The invention further proposes a process for forming a layer of diazonium salt on at least one surface, made of a conductive or semi-conductive material, of a substrate, characterized in that it comprises at least one step of electrografting at least one diazonium salt of general formula I below onto said at least one surface:

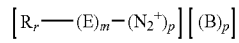

Formula I in which:
  R is a group which can be electrochemically reduced in a reversible manner at a cathode potential of between 0 and −1.5 V,
  E is a spacer chain consisting of at least one 5- to 6-membered aromatic cyclic group optionally containing one or more heteroatoms preferably chosen from N, S, O or P and optionally substituted with one or more groups chosen from $C_1$-$C_5$ alkyls and halogens,
  r is 0 or 1,
  m is an integer between 1 and 5 inclusive,
  p is an integer between 1 and 5, and
  B is a counterion.

Preferably, the layer formed has a thickness greater than 10 nm.

Preferably, B is chosen from a tosylate, sulfonate, halide or metal chloride group, more preferably B is $PF_6^-$ or $BF_4^-$.

Likewise preferably, R is chosen from a dicyanovinylidene, porphyrin, metal porphyrin, fullerene, metal bipyridine complex or quinone group, and a mixture thereof, more preferably R is a dicyanovinylidene group.

Preferably, the at least one compound of formula I is 2-diazonium-9-dicyanofluorenylidene tetrafluoroborate.

The process according to the invention can also comprise the electrografting of at least one second diazonium derivative which is not of formula I.

In this case, said at least second diazonium derivative is preferably chosen from 4-(heptadecafluorooctyl)benzenediazonium tetrafluoroborate, 4-(1,1,1,3,3,3-hexafluoro-2-hydroxypropan-2-yl)benzenediazonium tetrafluoroborate, and mixtures thereof.

In a first embodiment, the at least two compounds are electrografted one after the other.

However, the at least two compounds can also be electrografted simultaneously.

Finally, the invention proposes a diazonium salt, the cation of which is 2-diazonium-9-dicyanofluorenylidene and the anion of which is chosen from a tosylate, sulfonate, halide, metal chloride, hexafluorophosphate and tetrafluoroborate group.

Preferably, this diazonium salt is 2-diazonium-9-dicyanofluorenylidene tetrafluoroborate.

Figure 2:
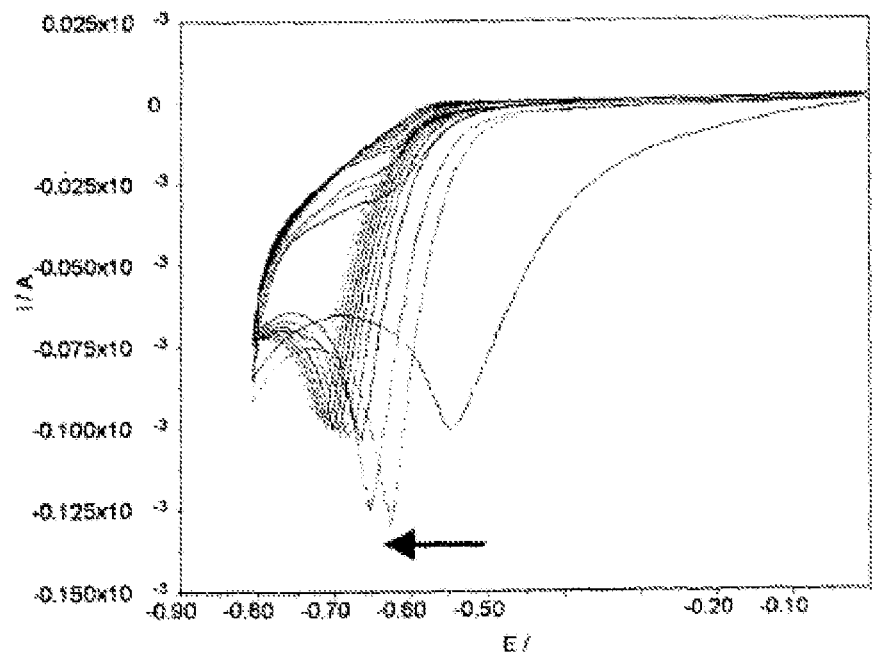
Figure 3:
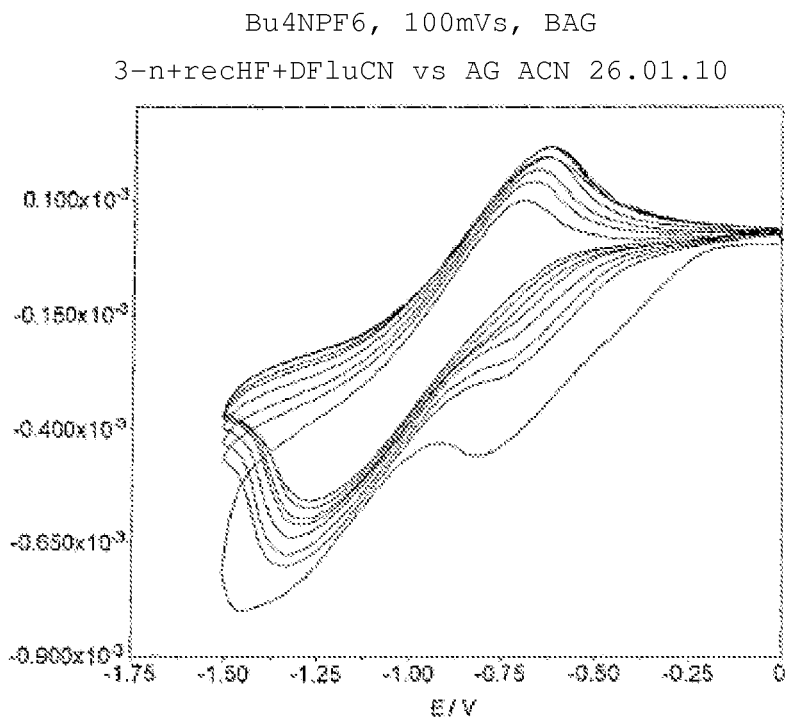
Figure 4:
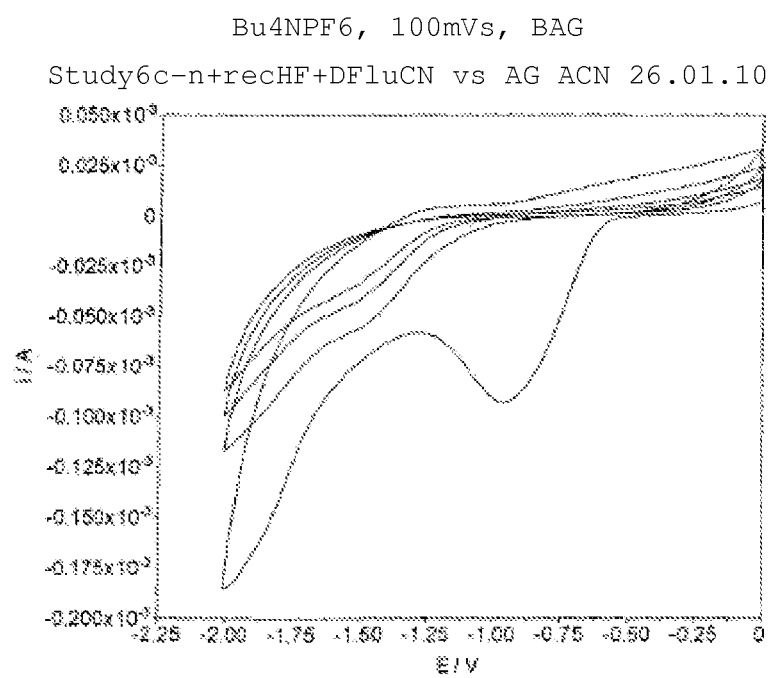
Figure 5:
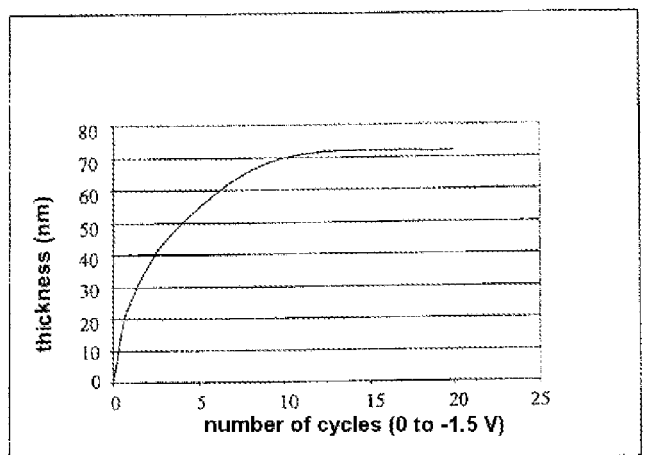
Figure 6:
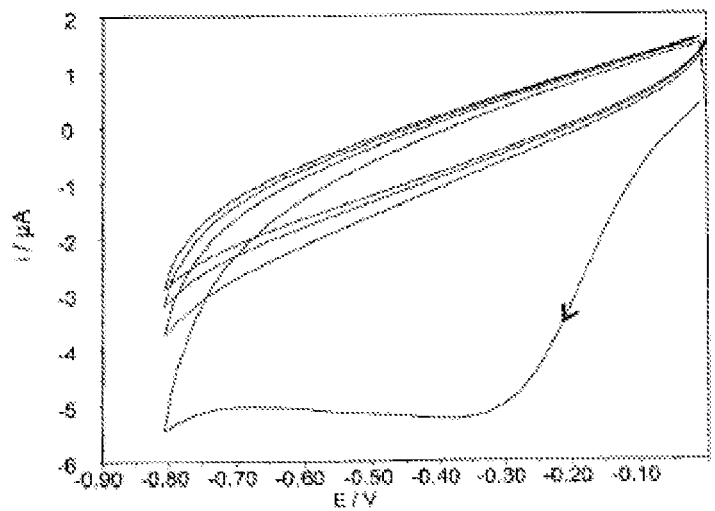
Figure 7:
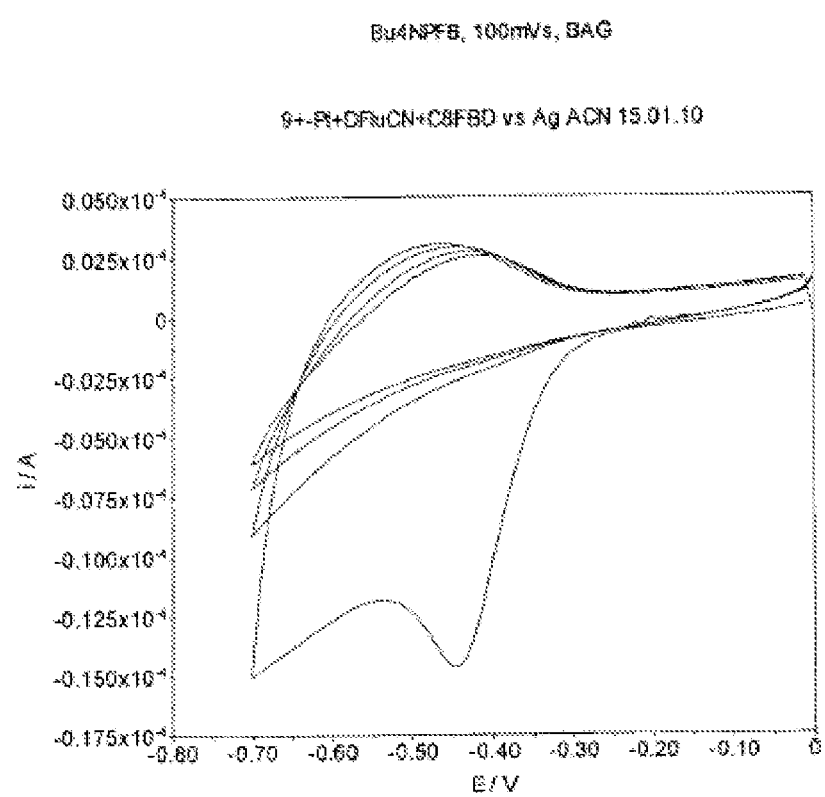

The invention will be understood more clearly and other advantages and characteristics thereof will emerge more clearly on reading the explanatory description which follows and which is given with reference to the figures in which:

FIG. 1 shows the curves obtained by cyclic voltammetry of the diazonium salt according to the invention on a platinum electrode, 5 mM in ACN (aceto-nitrile)+0.1 M $Bu_4NPF_6$, the electrode being obtained by electrografting of the diazonium salt of the invention in reduction via four cycles between 0.0 V and –1.0 V, FIG. 2 represents the curves obtained by cyclic voltammetry of the diazonium salt according to the invention electrografted in reduction via 25 cycles between 0.0 V and –0.8 V on a platinum electrode, 5 mM in ACN+0.1 M $Bu_4NPF_6$, FIG. 3 represents the curves of cyclic voltammetry of the diazonium salt according to the invention on a silicon electrode (n+, treated with hydrofluoric acid (HF)), ACN+0.1 M $Bu_4NPF_6$, obtained using a pseudo-reference electrode which is a silver wire at a scan rate of $0.1 \text{ V}\cdot\text{s}^{-1}$ with electrografting in reduction between 0.0 V and –1.5 V, FIG. 4 shows the cyclic voltammetry curves for boron-doped silicon ($10^{15}$ $cm^3$) treated with HF and modified with the diazonium salt according to the invention in ACN+0.1 M $Bu_4NPF_6$, using a silver wire as reference electrode, with a scan rate of $0.1 \text{ V}\cdot\text{s}^{-1}$, the surface having been modified by electrografting in reduction between 0.0 V and –1.5 V, FIG. 5 shows a curve representing the relationship between the thicknesses of surface modified with the diazonium salt of the invention and the number of electrografting cycles, FIG. 6 represents the cyclic voltammetry curves obtained during the electrografting of a diazonium salt of the prior art, 5 mM 4-heptadecafluorooctyl)benzenediazonium tetrafluoroborate (C8FBD), on a platinum electrode via successive scans between 0 and –0.8 V in ACN, 0.1 M $Bu_4NPF_6$ at a scan rate of $0.1 \text{ V}\cdot\text{s}^{-1}$ using a silver wire as pseudo-reference electrode, and FIG. 7 represents the curves obtained by cyclic voltammetry on a platinum electrode, in ACN+0.1 M $Bu_4NPF_6$, obtained after electrografting of the diazonium salt according to the invention followed by electrografting of the diazonium salt used in FIG. 6, using a silver wire as reference electrode, at a scan rate of $0.1 \text{ V}\cdot\text{s}^{-1}$, the electrografting of the diazonium salt according to the invention having been carried out in reduction between 0.0 V and –1.5 V and the post-electrografting of the diazonium salt used for FIG. 6 having been carried out between 0.0 V and –0.8 V.

The grafting of diazonium salts comprising a chemical group which is stable and electroactive in the cathode potentials, at a potential which makes it possible to activate the electroactive group without forming the anion resulting from the reduction of the phenyl radical formed from the diazonium salts, makes the grafted layer electron-conducting and a relay effect takes place from the electrode to the diazonium salts in solution, resulting in a possible over-grafting of an identical or different diazonium salt.

This relay effect can be represented as shown in the following scheme:

Scheme 1

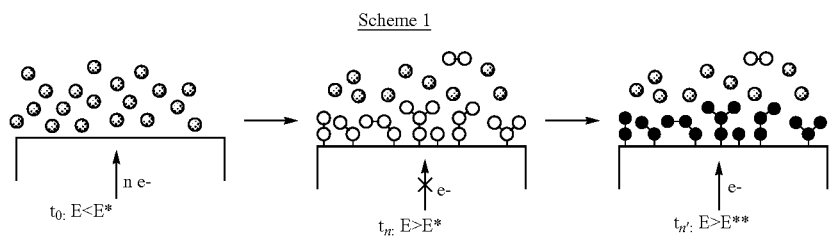

As represented in scheme 1, at the time $t_0$, the potential E applied to the substrate is less than the potential E* which is the threshold potential for reduction of the diazonium ion (in absolute value); the diazonium molecules are in solution (gray molecules).

At the time $t_n$, after application of a potential greater than the threshold potential E* for reduction of the diazonium salt (in absolute value), a transfer of electrons occurs from the surface of the substrate made of a conductive or semi-conductive material, which brings about the grafting of a certain number of diazonium salt molecules, onto the surface of the substrate (white molecules).

With the diazonium salts used in the invention, which will be described hereinafter, when a potential E** is reached resulting in the reduction of the electroactive groups of the diazonium salts used in the invention, at the time $t_n'$, the transfer of electrons is reestablished and the layer continues to grow.

In scheme 1 above, the black spheres represent the grafted molecules which are reduced at the potential E** resulting in reduction of the electroactive molecules.

Thus, the inventors have discovered that a novel family of diazonium salts can make it possible to obtain a relay effect at weakly cathodic potentials (0 to −1.5 V, in particular 0 to −1.0 V) and to grow the amount of diazonium salts deposited while at the same time preserving the stability of the electrode materials and of the deposited layer. This novel family of diazonium salts has 2-diazonium-9-dicyanofluorenylidene as cation and a group chosen from a tosylate, sulfonate, halide, metal chloride, hexafluorophosphate and tetrafluoroborate group as anion.

A salt of this family which is particularly preferred is 2-diazonium-9-dicyanofluorenylidene tetrafluoroborate (FLCND) or 2-diazonium(fluoren-9-ylidene)malononitrile tetrafluoroborate.

This diazonium salt has the following formula:

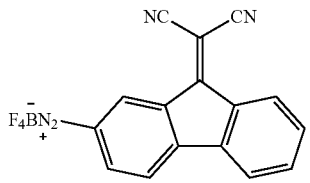

This compound is obtained in the following way:

It is possible to form 2-amino-9-dicyanofluorenylidene (AFLCN) or 2-amino(fluoren-9-ylidene)malononitrile from commercial 2-amino-9-dicyanofluorenone by means of a Knoevenagel reaction in the presence of malononitrile catalyzed by piperidine (black powder, yield 67). The amine function of the AFLCN compound subsequently enables the quantitative formation of the corresponding diazonium salt (FLCND) by reaction with nitrosonium tetrafluoroborate: 1 g of nitrosonium tetrafluoroborate $NOBF_4$ (8.56 mmol, 1.1 eq.) is placed in a round-bottomed flask dried under argon and is dissolved with 10 ml of anhydrous acetonitrile ACN. The whole mixture is brought to −30° C. using an acetone-liquid nitrogen bath and then 7.78 mmol of the arylamine precursor AFlCN, solubilized in the minimum amount of ACN (5 to 30 ml), are added dropwise. The mixture is allowed to return to ambient temperature, the product is precipitated from 100 ml of cold diethyl ether, filtered off on a frit and washed with cold ether. The yellow-ochre powder obtained is recrystallized with an ACN/$Et_2O$ mixture.

This family of salts and this diazonium salt, 2-diazonium-9-dicyanofluorenylidene tetrafluoroborate (FLCND), is a first subject of the invention.

It comprises a biphenyl group which makes it possible to easily carry out over-grafting on aromatic nuclei exhibiting little steric hindrance.

It also comprises a dicyanovinylidene group of formula:

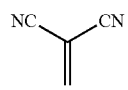

This group is one of the organic groups which exhibits reversible reduction, and which is the electroactive group.

The electrochemical analysis of the compound of the invention, in an anhydrous medium and on a platinum electrode, shows the very good stability of the reversible double reduction possible with this type of dicyanovinylidene function.

Scheme 2 below shows diagrammatically the reactions which occur.

Scheme 2

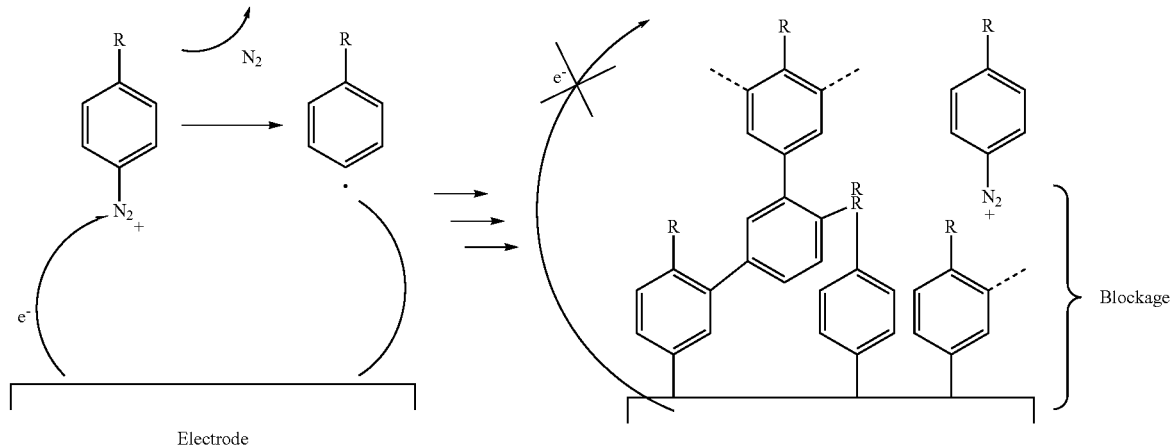

As is seen in scheme 2, there is formation of a grafted layer, said layer being grafted by covalent bonding, of molecules of formula I of which the diazonium group has disappeared, inhibiting electron transfer.

Moreover, it is seen from FIGS. 2 and 3 that the voltammogram obtained between 0 and −1.0 V with the diazonium salt of the invention grafted onto a platinum electrode in acetonitrile plus 0.1 M $Bu_4NPF_6$ and a reference electrode which is a silver wire, at a scan rate of 0.1 V·s$^{-1}$ shows electrografting.

Typically, the first scan toward the cathode potentials exhibits a nonreversible first wave (Ered=−0.54 V) corresponding to the reduction of the diazonium group and resulting in the modification of the surface of the electrode. The intensity of the current is proportional to the degree of transfer of electrons from the electrode to the solution (which depends on the electrode material, on the concentration of diazonium salt in solution and on the electrolyte). A second wave showing a peak potential at −0.91 V is obtained by scanning toward the more cathodic potentials. This wave corresponds to the dicyanovinylidene group activation potential and more particularly to the formation of the anion radical of the grafted salts and of the salts in solution, and shows reversibility (Eox=−0.79).

Usually, the grafting by means of the first cycle in reduction results in a passivating effect which is reflected by a zero faradic current in the range of potentials observed during the next scans. Here, the obtaining of the electron relay effect is visible for the subsequent scans. Thus, the additional reduction of the diazonium salts is possible and can be seen through a peak in reduction moving toward the cathode potentials (from −0.54 V to −0.73 V). Indeed, as soon as the threshold potential for reduction of the dicyanovinylidene groups is reached, the grafted layer becomes conductive and makes it possible to reactivate the electron transfer. A few cycles in reduction between 0.0 and −0.8 V are sufficient to obtain a golden deposit visible to the naked eye at the surface of the platinum electrode. The relay effect during the successive scans is much greater when the potential applied in reduction does not exceed the potential for formation of the anion radical of the cyanovinylidenes. If this threshold is reached, the subsequent scans show a strong decrease in the diazonium group reduction peak.

The compound of the invention can also be deposited on optionally doped silicon, or any other substrate consisting of a conductive or semi-conductive electrode material, in particular indium tin oxide (ITO), carbon-based materials, metals (Au, Ag, Ni, Cu, Pd, Co, W, Rh), indium, gallium, germanium, and semi-conductive metal oxides (Al-doped or Na-doped ZnO, F-doped $SnO_2$).

Silicon is the substrate of choice for the production of sensitive layers at the surface of sensors based on nano electromechanical systems (NEMS).

The covalent electro-depositing of the polymer obtained on the basis of the reduction of the compound of the invention (FLCND) was carried out on the various types of silicon n-doped with phosphorus or p-doped with boron and with charge carrier densities ranging from $10^{15}$ to $10^{19}$ carriers/$cm^3$ and on SOI (silicon on insulator) p-doped with boron with a charge carrier density of $10^{19}$ $cm^3$ with or without HF treatment (hydrofluoric acid intended to eliminate the native oxide of the silicon surface).

As is seen in FIG. 4, the cyclic voltammetry on a silicon electrode [(n+, treated with HF), ACN+0.1M $Bu_4NPF_6$, pseudo-reference electrode=silver wire, at scan rate v=0.1 V·s$^{-1}$] shows in the first scan an irreversible first peak (Ered=−0.81 V) identified as corresponding to the reduction of the diazonium group.

When scanning at more cathodic potentials, a new wave appears (Ered=−1.34 V) corresponding to the reversible system (Eox=−0.69 V) of the reduction of the dicyanovinylidenes to anion radicals.

During the subsequent scans, the presence of the diazonium group reduction peak is still visible (in the foot of the dicyano reduction wave). However, the intensity (and the amount of charge exchanged) decreases, showing that, after a few cycles, a saturation phenomenon is reached (which depends on the concentration of diazonium in the solution).

It should be noted that grafting operations by scanning at cathode potentials greater than −1.5 V give smaller deposits or even damaged deposits if −2.0 V is reached.

As for the case of the platinum electrode, the deposit is visible to the naked eye for all the silicon types tested. The polymer exhibits electrochromic properties: it is yellow when the potential for grafting onto silicon does not exceed the first dicyanovinylidene group reduction system and becomes blue if this potential is exceeded.

When the silicon wafers obtained by using the compound of the invention are examined with a scanning electron microscope or by AFM, it is noted that layers with a thickness of 50 nm are obtained.

The study of the surfaces of modified silicon gives the voltammograms shown in FIG. 5. A first wave (anion radical, Ered1=−1.0 to −1.13 V) is followed by a second (dianion, Ered2=−2.0 V) and signals the presence of the dicyanovinylidene groups.

The amounts of charges measured during the study of the modified surfaces (Q=300 to 1430 µC) indicate that 3.1 to 14.8×10$^{-9}$ mol of dicyanofluorenylidene are grafted. By considering the grafting density Γ=9×10$^{-10}$ mol·cm$^{-2}$, and by taking for the silicon electrode an area defined by $A_{Si}$=0.3 cm$^2$, a grafting equivalence of 11 to 55 layers is measured. If the thickness of a layer is taken to be equal to 0.8 nm (approximately), thicknesses of from 9 nm to 44 nm can be obtained if the deposit has a maximum compactness. Thus, in this case, a considerable proportion of the reduced diazonium salts is grafted at the surface of the electrode.

As is seen from FIG. 5, the AFM imaging of the modified surfaces obtained using the compound of the invention made it possible to determine that the thicknesses obtained were the following:
 1 cycle in reduction between 0.0 and −1.0 V of FLCND at a concentration of 2 mM results in a thickness of 25 nm;
 4 cycles result in a thickness of 50 nm and 10 cycles result in 70 nm.

The increase in the thickness is not linear with the cycle number and the thickness of 70 nm on silicon appears to be a threshold under the conditions used. The first scan is that which makes it possible to form the greatest relative thickness, it being possible to control said thickness by adjusting the concentration of the diazonium salt.

For comparison, a diazonium salt (5 mM) having the following formula was electrografted onto a platinum electrode:

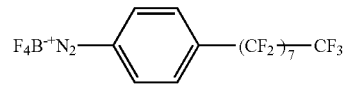

4-(heptadecafluorooctyl)benzenediazonium tetrafluoroborate (C8FBD)

The voltammograms obtained under the same conditions as for the diazonium salt of the invention (FLCND) are shown in FIG. 6.

It is seen from this FIG. 6 that the recurrent scans between 0 and −0.8 V of a 5 mM solution of C8FBD result in electrografting onto the platinum electrode. The first scan in cyclic voltammetry gives an irreversible peak at −0.35 V, corresponding to the reduction of the diazonium groups. Typically, the subsequent scans no longer show any faradic current: the electron transfer is inhibited by the modification of the electrode modified during the first scan.

The method for synthesizing the C8FBD compound is the following:
 1 g of nitrosonium tetrafluoroborate $NOBF_4$ (8.56 mmol, 1.1 eq.) is placed in a round-bottomed flask dried under argon and is dissolved with 10 ml of anhydrous acetonitrile (ACN), the whole mixture is brought to −30° C. by means of an acetone-liquid nitrogen bath, 7.78 mmol of the arylamine precursor solubilized in the minimum amount of ACN (5 to 30 ml) are then added dropwise, the mixture is left to return to ambient temperature, the product is precipitated from 100 ml of cold ether, it is filtered off on a frit, and it is washed with cold ether.

The white powder obtained is recrystallized with an ACN/Et$_2$O mixture.

Yield: 80%.

Moreover, in order to incorporate the chemical functions that are potentially advantageous for capturing VOCs, it is possible to carry out post-grafting operations or to perform a simultaneous reduction of various diazoniums contained in the same solution. This may also make it possible to incorporate molecules with high steric hindrance in order to obtain a greater porosity.

The simultaneous reduction of several diazonium precursors is more promising than post-grafting since most of the diazoniums are reduced after (at more cathodic potentials) the compound of the invention. Furthermore, it may be that the post-grafting takes place only at the surface of the preceding deposit if the molecule does not penetrate into the previously deposited FLCND layer.

Post-Grafting of C8FBD

The voltammograms shown in FIG. 7 prove that it is entirely possible to activate a diazonium salt (C8FBD) using a prior deposit of FLCND or by means of a co-electropolymerization.

In the case of post-grafting, the first cycle provides an immediate blocking effect when C8FBD is electrografted onto an electrode modified with a deposit of FLCND.

By way of comparison: C8FBD alone gives a peak at −0.35 V on platinum.

Simultaneous Reduction of C8FBD and FLCND

Various concentration ratios between FLCND and C8FBD were tested.

The electron transfer at the time of a 1/1 equimolar mixture (total diazonium concentration ~5 mM) is rapidly inhibited and no deposit is apparent at the surface of the electrode.

The results obtained show that, for a molar proportion of 12% of C8FBD (still for a total diazonium concentration of 5 mM), the blocking effect is achieved starting from the fourth cycle and no deposit is visible to the eye. On the other hand, with a molar proportion of 60 of C8FBD (still for a total diazonium concentration of 5 mM), the relay effect is preserved. The reduction peak is visible at each cycle and the reduction (after 20 cycles) makes it possible to obtain a golden deposit approximately 50 nm thick, visible at the surface of the electrode.

Simultaneous Reduction of HFHPBD and FLCND

A copolymerization of FLCND and HFHPBD was also tested.

HFHPBD has the following formula:

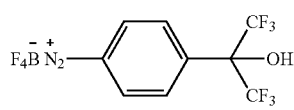

4-(1,1,1,3,3,3-hexafluoro-2-hydroxypropan-2-yl)
benzenediazonium

The groups carried by this molecule allow specific affinities with sarin gas derivatives and organophosphorus derivatives of DMMP (dimethyl methylphosphonate) type, simulating neurotoxic compounds according to the following scheme:

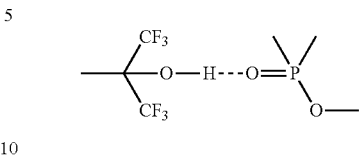

As for the coelectropolymerization with C8FBD, a decrease in the diazonium reduction peaks is obtained on the voltammograms after a few cycles for a molar proportion of 12% of HFHPBD. The ideal mixture for obtaining a thick deposit (with a thickness of approximately 50 nm) containing a maximum of secondary molecules (other than FLCND) lies in a proportion of from 5 to 10%.

For comparison: HFHPBD alone gives a peak at −0.63 V on platinum.

HFHPBD is synthesized in the following way:

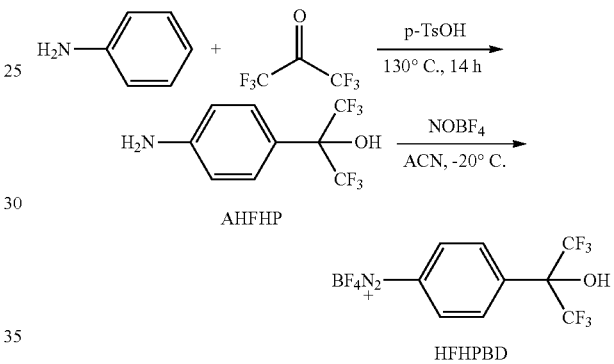

Aniline (10.35 ml, 0.1 mol) and 250 mg of p-toluenesulfonic acid catalyst are placed in a two-necked flask surmounted by a condenser. Hexafluoroacetone trihydrate is added dropwise (15.8 ml, 1.1 eq.) and the bath (graphite) is brought to 180° C. for 14 h. The product AHFHP (4-(1,1,1,3,3,3-hexafluoro-2-hydroxypropan-2-yl)aniline) is obtained by recrystallization from a dichloromethane/hexane mixture, in the form of a white powder (yield 52%). 1 g of nitrosonium tetrafluoroborate (NOBF$_4$) (8.56 mmol, 1.1 eq.) is then placed in a round-bottomed flask dried under argon and is dissolved with 10 ml of anhydrous acetonitrile ACN. The whole mixture is brought to −30° C. by means of an acetone-liquid nitrogen bath and then 7.78 mmol of the arylamine precursor, solubilized in the minimum amount of ACN (5 to 30 ml), are added dropwise. The mixture is allowed to return to ambient temperature, and the product is precipitated from 100 ml of cold ether, filtered off on a frit and washed with cold ether. The white powder obtained is recrystallized with an ACN/Et$_2$O mixture and obtained with a yield of 64%.

The electrografting of organic layers on the basis of the reduction of diazonium salts is a preferred approach for localized functionalization that can be carried out on an NEMS scale. The results of the electrografting (layer thickness, potentials to be applied) depend both on the electronic and steric parameters of the molecules used and on the conductivity parameters of the substrates linked to the surface effects. The electrografting of diazoniums is a self-limiting process which makes it possible to form layers of small thicknesses. To improve the deposit thickness and in the context of the production of sensitive layers for detecting volatile molecules, a strategy for the controlled production of organic layers of several tens of nanometers has been developed. Said strategy consists in increasing the possibility of growth of the layer formed by the reduction of diazonium salts by electrochemically activating a dicyanovinylidene function. The cathodic coelectropolymerization of various diazonium salts including specific organic substituents also makes it possible to form large deposits with a controlled thickness so as to make it possible to improve the sensitivity of detection in the case of the functionalization of NEMS or other transducers.

Thus, although in the aforementioned, the diazonium salt FLCND and its use, optionally in combination with the diazonium salts C8FBD and HFHPBD, was described, it will be clearly apparent to those skilled in the art that the invention is in no way limited to this compound and to the use of this compound, optionally in combination with other diazonium salts, for forming layers with a thickness greater than 10 nm, grafted at the surface of a substrate made of a conductive or semi-conductive material, but that any compound, taken alone or as a mixture, having formula I below can also be used:

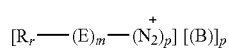

Formula I

Thus, the invention relates to the use of a compound of general formula I below:

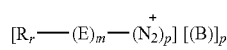

Formula I in which:
R is a group which can be electrochemically reduced in a reversible manner at a cathode potential of between 0 and −1.5 V and preferably greater in absolute value than the activation potential of the $N_2^+$ ion,
r is chosen between 1 and 2,
E is a spacer chain consisting of at least one 5- or 6-membered aromatic cyclic group optionally containing one or more heteroatoms preferably chosen from N, S, O and P and optionally substituted with one or more groups chosen from $C_1$-$C_5$ alkyls and halogens,
m is an integer between 1 and 5 inclusive,
p is an integer between 1 and 5 inclusive, and
B is a counterion,
for the formation, by electrografting, of a layer on a surface of a substrate made of a conductive or semiconductive material.

Preferably, this layer has a thickness greater than 10 nm.

B is preferably chosen from a tosylate, sulfonate, halide, metal chloride (½$ZnCl_2$, etc.) group and is more preferably a $PF_6^-$ or $BF_4^-$ (hexafluorophosphate or tetrafluoroborate) anion.

With regard to the R group, it is a group which can be electrochemically reduced in a reversible manner at a cathode potential of between 0 and −1.5 V.

R is preferably chosen from a dicyanovinylidene, porphyrin, metal porphyrin, fullerene, metal bipyridine complex or quinone group, and a mixture thereof.

The porphyrin groups that can be used in the invention are in particular 5-(4-aminophenyl)-10,20-bis(2,4,6-trimethylphenyl)porphyrin described in Liddell et al., "Porphyrin-Based Hole Conducting Electropolymer", Chem. Mater. 2008, 20, 135-142 and tetraphenylporphyrin (TPP), octaethyltetraphenylporphyrin ($Et_8TPP$ or OETPP), octabromotetraphenylporphyrin ($Br_8TPP$) and (pentafluorophenyl)octabromotetraphenylporphyrin ($Br_8F_{20}TPP$), described by Kadish et al., in "Electrochemistry of porphyrins and related macrocycles" J Solid State Electrochem (2003) 7:254-258.

The metal porphyrin groups that can be used in the invention are, for example, the zinc(II) tetra-kis(pentafluorophenyl)porphyrin described by Hodge et al., in "Electrochemistry of Nonplanar Zinc(II) tetra-kis(pentafluorophenyl)porphyrins", Inorg. Chem. 1995, 34, 809-812.

The fullerene groups that can be used as R group in the invention are, in particular, spiromethanofullerenes, iminofullerenes and fluorofullerenes and also the $C_{120}O$ and $^{45}C_{60}$ fluorene dimers described by Echegoyen et al., in "Electrochemistry of Fullerenes and Their Derivatives", Acc. Chem. Res. 1998, 31, 593-601, and also the N-Mteg-fulleropyrrolidine and C-mTEG-pyrrolidine (TEG=triethylene glycol) described by Carano et al., in "Electrochemical properties of soluble fullerene derivatives" Electrochemical Acta 46 (2000) 265-269.

As quinones that can be used in the invention, mention may be made of the 3,5-di-cert-butyl-1,2-benzoquinone described by Lehmann et al., in "Mechanism of the Electrochemical Reduction of 3,5-di-tert-butyl-1,2-benzoquinone. Evidence for a Concerted Electron and Proton Transfer Reaction Involving a Hydrogen-Bonded Complex as Reactant", J. Phys. Chem. B 2001, 105, 8877-8884.

As compound of formula I in which the R group is a metal bipyridine complex, mention may be made of the diazonium salts [Ir(phenylpyridine)$_2$(bipyridine-phenyl-$N_2^+$)][$PF_6$]$_2$ and [Ru(bipyridine)$_2$(bipyridine-phenyl-$N_2^+$)][$PF_6$]$_3$ described in European patent application No. 1921084 A1.

Other complexes of metal bipyridine type that can be used in the invention are 2,3-bis(2-pyridyl)pyrazine and 2,5-bis(2-pyridyl)pyrazine described by Marcaccio et al., in "Electrochemistry of Multicomponent Systems. Redox Series Comprising up to 26 Reversible Reduction Processes in Polynuclear Ruthenium(II) Bipyridine-Type Complexes" J. Am. Chem. Soc. 1999, 121, 10081-10091 and 4,6-bis(2',2"-bipyrid-6'-yl)-2-phenylpyrimidine described by Ruben et al., in "Multilevel Molecular Electronic Species Electrochemical Reduction of a [2×2] $CO_4^{II}$ Grid-Type Complex by 11 Electrons in 10 Reversible Steps" Angew. Chem. Int. Ed. 2000, 39, No. 22, pages 4139-4141.

However, it is most particularly preferred to use, in the invention, an R group which is a dicyanovinylidene group.

In addition, it is most particularly preferred to use a compound of formula I which is 2-diazonium-9-dicyanofluorenylidene tetrafluoroborate, alone or in combination with another diazonium salt, in particular the diazonium salts 4-(heptadecafluorooctyl)benzenediazonium tetrafluoroborate or 4-(1,1,1,3,3,3-hexafluoro-2-hydroxypropan-2-yl)benzenediazonium tetrafluoroborate.

Through the use of these salts, it is possible, according to the invention, to obtain a substrate comprising at least one surface made of a conductive or semi-conductive material, such as platinum, optionally doped silicon, or any other substrate consisting of a conductive or semi-conductive electrode material, in particular ITO, carbon-based materials, metals (Au, Ag, Ni, Cu, Pt, Pd, Co, W, Rh), indium, gallium, germanium and semi-conductive metal oxides (Al-doped or Na-doped ZnO, F-doped $SnO_2$), onto which surface 9-dicyanofluorenylidene molecules are grafted.

This substrate is particularly suitable for the manufacture of a sensor for detecting and/or quantifying gas compounds and/or volatile organic compounds (VOCs).

This substrate can therefore advantageously be integrated into a device for detecting and/or quantifying gas compounds and/or volatile organic compounds (VOCs).

Consequently, another subject of the invention is a process for forming a layer of diazonium salt on at least one surface made of a conductive or semiconductive material of a substrate, comprising at least one step of electrografting at least one diazonium salt of general formula I below onto said at least one surface:

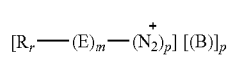

Formula I in which:
- R is a group which can be electrochemically reduced in a reversible manner at a cathode potential between 0 and −1.5 V,
- E is a spacer chain consisting of at least one 5- to 6-membered aromatic cyclic group optionally containing one or more heteroatoms preferably chosen from N, S, O or P and optionally substituted with one or more groups chosen from $C_1$-$C_5$ alkyls and halogens,
- r is 1 or 2,
- m is an integer between 1 and 5 inclusive,
- p is an integer between 1 and 5, and
- B is a counterion.

By virtue of this process, a layer with a thickness greater than 10 nm is formed, by electrografting, on a surface of a substrate made of a conductive or semiconductive material.

In this process, B is preferably chosen from a tosylate, sulfonate, halide or metal chloride (½$ZnCl_2$, etc.) group. More preferably, B is $PF_6^-$ or $BF_4^-$ (hexafluorophosphate or tetrafluoroborate).

With regard to R, it is preferably chosen from a dicyanovinylidene, porphyrin, metal porphyrin, fullerene, metal bipyridine complex or quinone group, and a mixture thereof.

More preferably, R is a dicyanovinylidene group.

In one particular embodiment, at least two compounds which are diazonium derivatives are electrografted, at least one of which corresponds to formula I.

In this same particular embodiment of the invention, the compound of formula I is 2-diazonium-9-dicyanofluorenylidene tetrafluoroborate.

Still in this particular embodiment of the invention, one of the diazonium derivative compounds is chosen from 4-(heptadecafluorooctyl)benzenediazonium tetrafluoroborate and 4-(1,1,1,3,3,3-hexafluoro-2-hydroxypropan-2-yl)benzenediazonium tetrafluoroborate.

Preferably, the at least two compounds are electrografted simultaneously.

However, they can also be electrografted successively, beginning with the compound of formula I.

The invention claimed is:

1. A process for forming a layer of diazonium salt on at least one surface, made of a conductive or semi-conductive material, of a substrate, characterized in that it comprises at least one step of electrografting at least one diazonium salt of general formula I below onto said at least one surface:

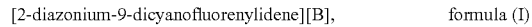

in which B is $PF_6^-$ or $BF_4^-$, for the formation, by electrografting, of a layer on a surface of a substrate made of a conductive or semi-conductive material.

2. The process as claimed in claim 1, characterized in that it also comprises the electrografting of at least one second diazonium derivative which is not of formula I.

3. The process as claimed in claim 1, characterized in that said at least second diazonium derivative is chosen from 4-(heptadecafluorooctyl)benzenediazonium tetrafluoroborate, 4-(1,1,1,3,3,3-hexafluoro-2-hydroxypropan-2-yl)benzenediazonium tetrafluoroborate, and mixtures thereof.

4. The process as claimed in claim 1, characterized in that the at least two compounds are electrografted one after the other.

5. The process as claimed in claim 1, characterized in that the at least two compounds are electrografted simultaneously.

* * * * *